United States Patent
Mitchell et al.

(10) Patent No.: US 11,497,538 B2
(45) Date of Patent: Nov. 15, 2022

(54) WOVEN OR BRAIDED TUBULAR METAL CONSTRUCT

(71) Applicant: FORT WAYNE METALS RESEARCH PRODUCTS CORP, Fort Wayne, IN (US)

(72) Inventors: Robert A. Mitchell, Huntington, IN (US); Mark Michael, Corunna, IN (US)

(73) Assignee: Fort Wayne Metals Research Products, LLC, Fort Wayne, IN (US)

( * ) Notice: Subject to any disclaimer, the term of this patent is extended or adjusted under 35 U.S.C. 154(b) by 0 days.

(21) Appl. No.: 16/069,643

(22) PCT Filed: Jan. 20, 2017

(86) PCT No.: PCT/US2017/014355
§ 371 (c)(1),
(2) Date: Jul. 12, 2018

(87) PCT Pub. No.: WO2017/127692
PCT Pub. Date: Jul. 27, 2017

(65) Prior Publication Data
US 2019/0015142 A1  Jan. 17, 2019

Related U.S. Application Data

(60) Provisional application No. 62/286,062, filed on Jan. 22, 2016.

(51) Int. Cl.
*A61B 17/82* (2006.01)
*A61F 2/90* (2013.01)
(Continued)

(52) U.S. Cl.
CPC .......... *A61B 17/826* (2013.01); *A61B 17/823* (2013.01); *A61B 17/842* (2013.01);
(Continued)

(58) Field of Classification Search
CPC ..... A61B 17/82; A61B 17/826; A61B 17/823; D04C 1/06; D04C 1/02; D03D 3/02; D02D 15/00
See application file for complete search history.

(56) References Cited

U.S. PATENT DOCUMENTS 3,125,095 A * 3/1964 Kaufman et al. ............................ A61B 17/06166
606/228
4,184,784 A * 1/1980 Killian .................... F16G 11/05
24/122.6
(Continued)

FOREIGN PATENT DOCUMENTS

JP 2002511281 A 4/2002
JP 2014161650 A 9/2014
(Continued)

OTHER PUBLICATIONS

International Search Report and Written Opinion, dated Apr. 14, 2017 in corresponding International Patent Application No. PCT/US2017/014355.
(Continued)

*Primary Examiner* — Christopher J Beccia
(74) *Attorney, Agent, or Firm* — Faegre Drinker Biddle & Reath LLP

(57) ABSTRACT

Multi-filament microcables are used in place of the traditional monofilament wires as the constituent elements of a woven or braided band. This enhances the function and manufacturability of such bands for various applications, such as orthopaedic applications including sternotomy closures.

16 Claims, 6 Drawing Sheets

(51) Int. Cl.
| | |
|---|---|
| *D04C 1/02* | (2006.01) |
| *D04C 1/06* | (2006.01) |
| *A61L 31/02* | (2006.01) |
| *A61L 31/14* | (2006.01) |
| *D03D 1/00* | (2006.01) |
| *D02G 3/12* | (2006.01) |
| *A61B 17/84* | (2006.01) |
| *D03D 15/25* | (2021.01) |
| *A61F 2/08* | (2006.01) |
| *D03D 3/02* | (2006.01) |
| *A61B 17/00* | (2006.01) |

(52) U.S. Cl.
CPC .............. *A61F 2/0811* (2013.01); *A61F 2/90* (2013.01); *A61L 31/022* (2013.01); *A61L 31/14* (2013.01); *A61L 31/148* (2013.01); *D02G 3/12* (2013.01); *D03D 1/00* (2013.01); *D03D 3/02* (2013.01); *D03D 15/25* (2021.01); *D04C 1/02* (2013.01); *D04C 1/06* (2013.01); *A61B 2017/00862* (2013.01); *A61F 2002/0852* (2013.01); *A61F 2210/0004* (2013.01); *A61F 2210/0014* (2013.01); *A61F 2220/0033* (2013.01); *A61L 2400/16* (2013.01); *D10B 2101/20* (2013.01); *D10B 2401/12* (2013.01); *D10B 2509/04* (2013.01); *D10B 2509/06* (2013.01)

(56) References Cited

U.S. PATENT DOCUMENTS

| | | | |
|---|---|---|---|
| 5,541,380 A | 7/1996 | Ogden et al. | |
| 5,755,704 A * | 5/1998 | Lunn | A61M 25/0012 600/585 |
| 6,342,068 B1 | 1/2002 | Thompson | |
| 6,494,907 B1 | 12/2002 | Bulver | |
| 8,152,833 B2 * | 4/2012 | Zaver | A61F 2/0105 606/200 |
| 2005/0267568 A1 | 12/2005 | Berez et al. | |
| 2007/0208373 A1 | 9/2007 | Zaver et al. | |
| 2008/0119892 A1 * | 5/2008 | Brailovski | A61B 17/82 606/215 |
| 2011/0079315 A1 * | 4/2011 | Norton | D04C 1/06 140/71 R |
| 2011/0319978 A1 | 12/2011 | Schaffer | |
| 2012/0109129 A1 * | 5/2012 | Bernstein | A61B 17/823 606/74 |
| 2014/0088688 A1 * | 3/2014 | Lilburn | D04C 1/06 623/1.15 |
| 2015/0045908 A1 | 2/2015 | McMahon | |
| 2015/0182674 A1 | 7/2015 | Schaffer | |

FOREIGN PATENT DOCUMENTS

| | | |
|---|---|---|
| WO | 2011093608 | 4/2011 |
| WO | 2017127692 A1 | 7/2017 |
| WO | 2012099910 A2 | 7/2021 |

OTHER PUBLICATIONS

Partial Supplementary European Search Report, dated Aug. 8, 2019 in corresponding European Patent Application No. 17742019.7.
International Preliminary Report on Patentability received for PCT Patent Application No. PCT/US2017/014355, dated Aug. 2, 2018, 7 pages.
Office Action dated Aug. 19, 2020 in corresponding Chinese Application No. 201780007543.8, with language translation.
Office Action dated Apr. 3, 2020 in corresponding Chinese Application No. 201780007543.8, with English language translation.

* cited by examiner

WOVEN OR BRAIDED TUBULAR METAL CONSTRUCT

CROSS-REFERENCE TO RELATED APPLICATIONS

The present application is a national phase filing under 35 U.S.C. § 371 of International Application No. PCT/US2017/014355, titled "WOVEN OR BRAIDED TUBULAR METAL CONSTRUCT," filed on Jan. 20, 2017, which claims the benefit of priority to U.S. Provisional Application No. 62/286,062, filed on Jan. 22, 2016, the entire disclosures of which are hereby expressly incorporated herein by reference.

BACKGROUND

1. Technical Field

The present disclosure is directed to woven or braided bands and, in particular, to woven or braided metal bands configured for use in high-strength surgical suture applications such as sternotomy closures.

2. Description of the Related Art

Woven or braided hollow tubes made of, e.g., metal or polymer materials are sometimes used for orthopedic applications, such as sternotomy closures. Such closures present unique challenges owing to potentially large movements in the vicinity of the incision as the patient moves, and the attendant large forces which may be placed upon the sutures.

In order to prevent damage to the bone, these woven or braided structures are adapted to lay flat against the bone in order to spread the pressure from axial tension. Other such closures may be made from a flat band of material, which also reduces the force on adjacent bone or other tissue provided the flat surface of the band is the contacting surface.

What is needed is an improvement over the foregoing.

SUMMARY

The present disclosure is directed to multi-filament microcables used in place of the traditional monofilament wires as the constituent elements of a woven or braided band. This enhances the function and manufacturability of such bands for various applications, such as orthopaedic applications including sternotomy closures.

In one form thereof, the present disclosure provides a multifilament tubular construct, including: a plurality of constituent elements woven or braided into a tubular construct defining an inner diameter, an outer diameter and an axial length in the absence of external forces, the constituent elements each including: a plurality of metal filaments having respective longitudinal axes running substantially parallel to one another.

In one aspect, the constituent elements are twisted cables in which the longitudinal axes of the plurality of metal filaments each define helices running substantially parallel to one another.

In another aspect, the plurality of metal filaments of the constituent elements comprises between 2 filaments and 343 filaments.

In another aspect, the inner diameter of the tubular construct is between 0.010 inches and 0.200 inches, and/or the outer diameter of the tubular construct is between 0.014 inches and 0.208 inches.

In another aspect, the plurality of constituent elements comprises between 8 and 128 constituent elements.

In another aspect, the plurality of constituent elements define a plurality of picks at respective points of intersection between neighboring constituent elements, the picks numbering between 1 and 50 per inch of axial distance along an outer surface of the tubular construct.

In another aspect, the construct further includes at least one friction-fit fitting formed on an end of the tubular construct. In one example, the friction-fit fitting cannot be dislodged from the tubular construct by a separation force less than 142 lbf.

In yet another aspect, at least one of the plurality of metal filaments of the constituent elements is formed of an absorbable metal, such as at least one of magnesium, zinc, iron and alloys thereof.

In still another aspect, at least one of the plurality of metal filaments of the constituent elements is formed of stainless steel and/or a superelastic alloy such as Nitinol, and/or a cobalt-based alloy, and/or a cobalt-chrome alloy.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1A:
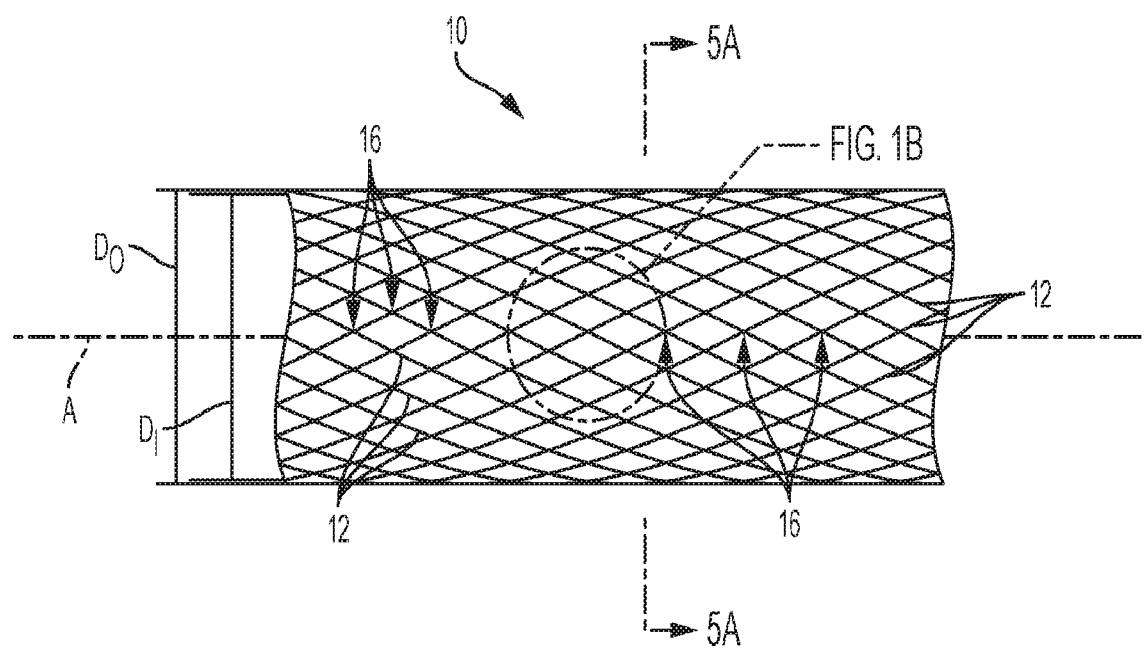
FIG. 1A is an elevation view of a braided tubular construct made in accordance with the present disclosure.

Corresponding reference characters indicate corresponding parts throughout the several views. Although the exemplifications set out herein illustrate embodiments of the invention, the embodiments disclosed below are not intended to be exhaustive or to be construed as limiting the scope of the invention to the precise form disclosed.

DETAILED DESCRIPTION

Introduction

Figure 1B:
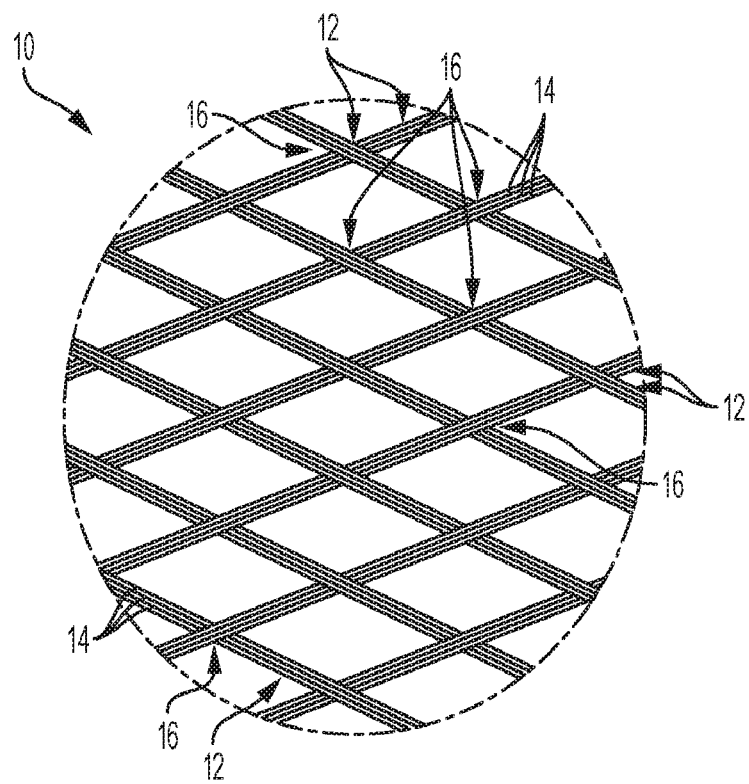
FIG. 1B is an enlarged elevation view of a portion of FIG. 1, illustrating individual stranded cables making up the constituent elements of the braided tubular construct.
Figure 2:
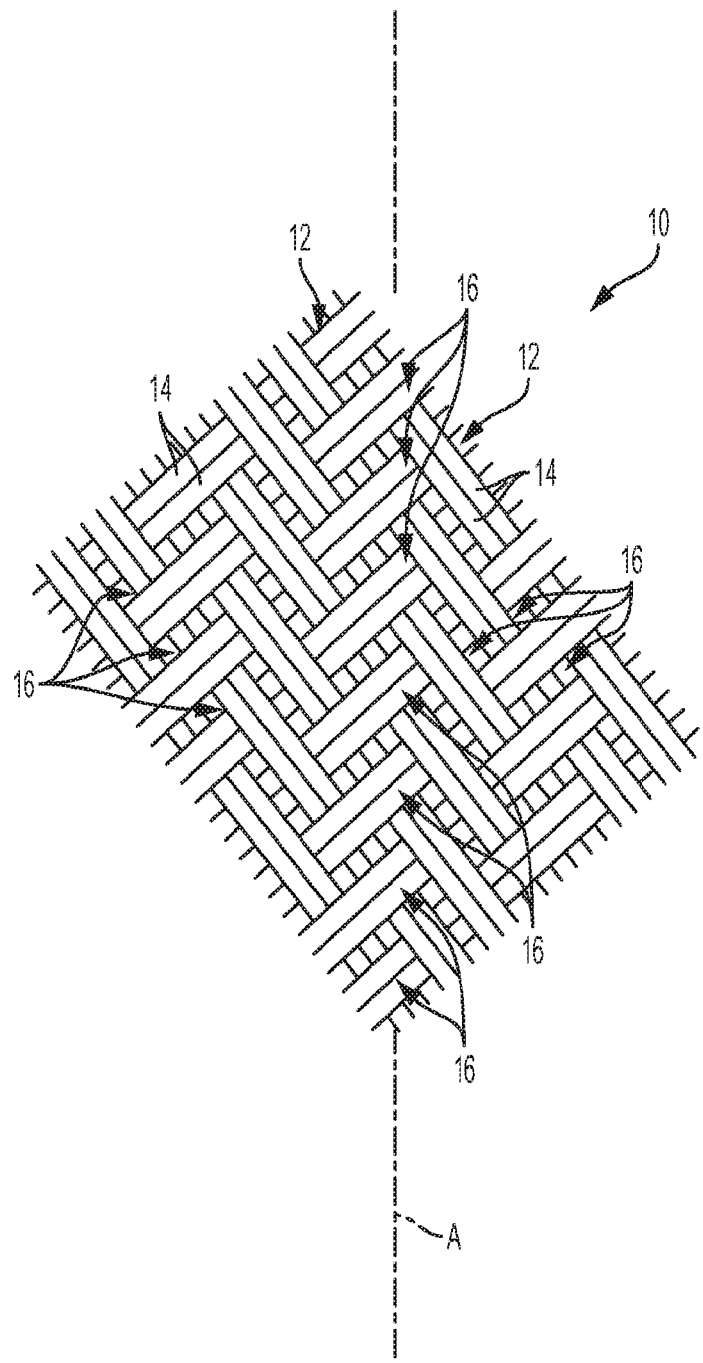
FIG. 2 is a schematic view illustrating an exemplary braid pattern used in the braided tubular construct of FIG. 1A.
Figure 5B:
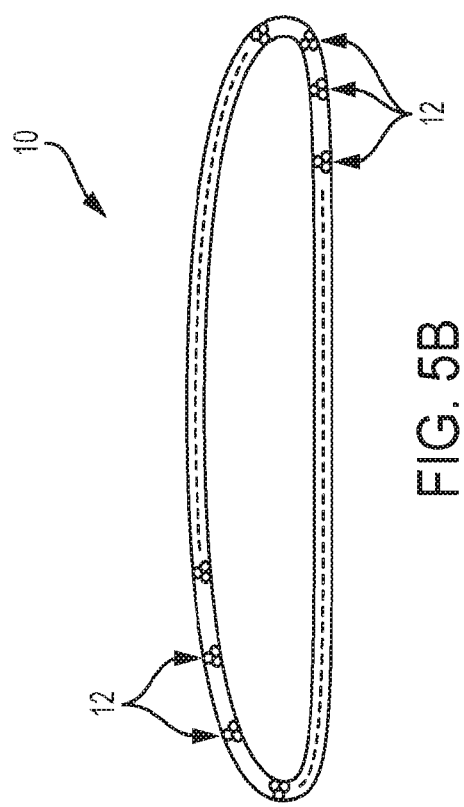
FIG. 5B is another cross-section, elevation view of the braided tubular construct of FIG. 5A, illustrating a "flattening" deformation when the construct is bent or compressed around a surface.
Figure 5A:
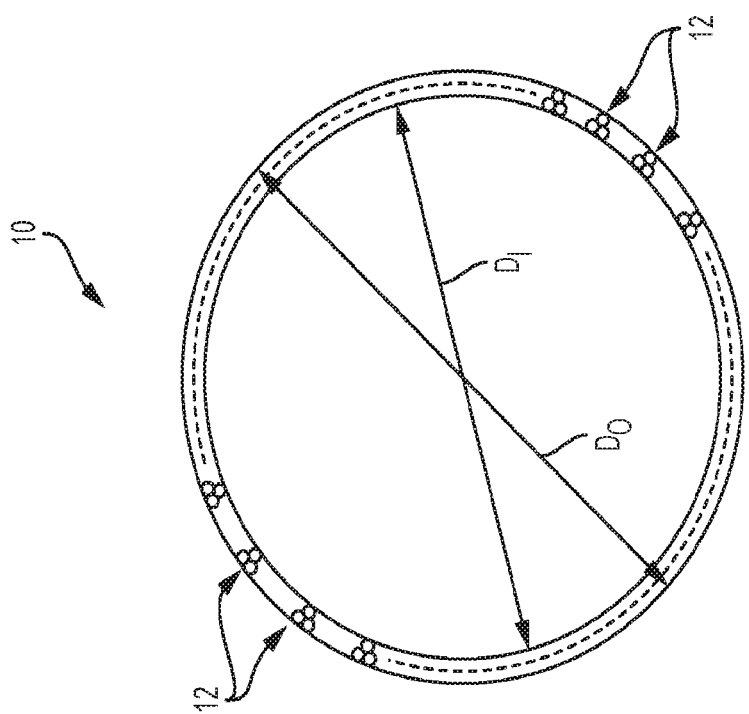
FIG. 5A is an cross-section, elevation view of the braided tubular construct of FIG. 1, taken along line 5A-5A of FIG. 1, shown in a free state without any external forces applied.

The present disclosure provides a braided or woven tubular construct 10, shown in FIG. 1, in which the individual constituent elements 12 are stranded cables consisting of a plurality of twisted strands 14 (FIG. 2). As described in further detail below, the utilization of such multi-strand constituents 12 in construct 10 provides a smooth texture or "hand" which facilitates the use of construct 10 in orthopaedic and other medical applications, provides a large surface-area contact with adjacent bone or tissue when construct 10 lays flat (FIG. 5B), and allows for high-strength crimp attachments at the ends of construct 10.

In one exemplary embodiment, for example, a multi-strand braided band 10 is made from a number of multi-strand constituent cables 12 having an overall diameter of 0.0075 inches. Such a design may be compatible with existing tools and orthopaedic devices designed for use with an existing monofilament-constituent braid with individual wires having a diameter of 0.0051 inches, such that band 10 can be used with an ecosystem of industry-standard orthopaedic devices and connectors. However, band 10 may use forty-eight stranded cables 12 having seven wires per stranded cable 12 for a total of 224 individual monolithic strands 14, rather than using forty-eight monofilament wires for the completed woven construct. This increase in the number of wires, and attending decrease in the diameter of each individual strand 14, has been found to offer significant performance advantages as further described herein.

Terminology

As used herein, "wire" or "wire product" encompasses continuous wire and wire products which may be continuously produced and wound onto a spool for later dispensation and use, such as wire having a round cross section and wire having a non-round cross section, including flat wire or ribbon. "Wire" or "wire product" also encompasses other wire-based products such as strands, cables, coil, and tubing, which may be produced at a particular length depending on a particular application. In some exemplary embodiments, a wire or wire product in accordance with the present disclosure may have a diameter up to 2.5 mm.

"Nitinol" is a trade name for a shape memory alloy comprising approximately 50 atomic % Nickel and balance Titanium, also known as NiTi, commonly used in the medical device industry for highly elastic implants. One exemplary NiTi material is described in U.S. Pat. No. 8,840,735, filed Sep. 18, 2009 and entitled "Fatigue Damage Resistant Wire and Method of Production Thereof," the entire disclosure of which is hereby expressly incorporated by reference herein.

"Impurities," "incidental impurities" and "trace impurities" are material constituents present in a material at less than 500 parts per million or 0.05 wt. %.

"DFT®" is a registered trademark of Fort Wayne Metals Research Products Corp. of Fort Wayne, Ind., and refers to a bimetal or poly-metal composite wire product including two or more concentric layers of metals or alloys, typically at least one outer layer disposed over a core filament formed by drawing a tube or multiple tube layers over a solid metallic wire core element. The structure and processing of DFT materials is described in U.S. Patent Application Publication No. 2011/0319978, filed Jun. 24, 2011 and entitled "Biodegradable Composite Wire for Medical Devices," the entire disclosure of which is hereby expressly incorporated by reference herein.

As used herein, "fatigue strength" refers to the load level at which the material meets or exceeds a given number of load cycles to failure. Herein, the load level is given as alternating strain, as is standard for displacement or strain-controlled fatigue testing, whereby terms are in agreement with those given in ASTM E606, the entirety of which is incorporated herein by reference.

Braid Construction and Characteristics

Braided tubular construct 10, shown in FIG. 1A, includes a number of constituent elements 12 which cooperate to form a generally tubular construct defining outer diameter $D_O$ and inner diameter $D_I$, and longitudinal axis A. In particular, each element 12 is wound around a mandrel (not shown) during production to form a helix, and the respective constituent elements 12 are interwoven or braided with one another such that a regular overlapping pattern of criss-crossing helices is formed to create the finished tubular construct 10. In many applications, construct 10 is an inherently flexible structure in both an axial direction (i.e., the axial length of construct can be "stretched" or "compressed" by a force applied along longitudinal axis A) and a radial direction (i.e., longitudinal axis A may be "bent" into a rounded or non-linear form). For purposes of the present disclosure, diameter $D_O$, diameter $D_I$, and the axial length of construct 10 in the finished form are measured when construct 10 is in a "free state" in which no external forces are applied and the overall shape and size of construct 10 is dictated by the form of its braid or weave, the material of its constituent elements 12, and any processing such as heat treatment (described further below).

FIG. 1B illustrates that each element 12 includes a number of individual filaments or strands 14 which run parallel to one another. For purposes of the present disclosure, a "filament" is a single or monolithic fiber, while a "strand" may either be a monolithic fiber or a bundle of such fibers. Except as otherwise specified herein, a "strand" refers to a monolithic fiber (i.e., a filament).

For example, FIG. 1B illustrates strands 14 as straight filaments having a longitudinal axis parallel to the neighboring strands 14 of a given element 12. In another exemplary embodiment, elements 12 are formed as multi-strand (i.e., multi-filament) cables including a plurality (i.e., at least two) of strands 14 twisted around one another. In such a twisted-cable design, each strand 14 of a respective element 12 forms a helix that runs substantially parallel to the helices of the neighboring strands, such that the longitudinal axes of each strand 14 in a given element 12 run parallel one another.

Each junction between two of elements 12 is referred to herein as a pick 16, such that a "tightness" of the braid pattern can be expressed as a number of picks 16 per unit of axial length. One exemplary embodiment of a braid pattern for tubular construct 10 is illustrated in FIG. 2. As shown, each element 12 includes two straight, parallel strands 14. Each element 12 of the braid pattern passes over two neighboring elements, then under two neighboring elements, repeating this pattern for the entire extent of construct 10. Longitudinal axis A is illustrated at a 45-degree angle to the criss-crossing longitudinal axes of elements 12 (and strands 14), with seven picks 16 illustrated along the illustrated axial portion of construct 10. Other braid patterns may also be used as required or desired for a particular application. Examples of suitable braid patterns include full, diamond, and half patterns. In an exemplary embodiment, any machine-braidable pattern may be used in order to create a high throughput of braided material for constructs 10.

The braid or weave configuration may be altered as required or desired for a desired application. In an exemplary embodiment, at least eight discrete constituent elements 12 are used to create construct 10, through it is possible to use as few as four constituent elements 12. As many as 64 or 128 constituent elements 12 may be used, or any number between four and 128 as needed. In general, a larger number of elements 12 promotes a "denser" braid, i.e., a braid with relatively more picks 16 per inch as compared to a "loose" or "sparse" braid with fewer elements 12. In an exemplary embodiment, picks 16 may number as few as one per inch and as many as 50 per inch. A relatively small density of picks 16 contributes to a smooth feel or "hand" while a higher density of picks 16 is somewhat more abrasive.

FIGS. 3A-3G show various additional cross-sectional configurations of strands 14 to form elements 12 of construct 10. For purposes of the present discussion, FIGS. 3A-3G are drawn to a common scale relative to one another, such that the effective outer diameters $D_C$ of elements 12A-12G are all substantially equal. As illustrated by a comparison of FIGS. 3A-3G, the diameter of individual strands 14 get smaller as the number of strands 14 used in elements 12A-12G grows. Although FIGS. 3A-3G illustrate several exemplary configurations of multi-strand elements 12, it is contemplated that other configurations consistent with the principles of wire rope construction may be used as required or desired for a particular application. In general, a higher number of strands 14 for a given diameter $D_C$ of element 12 imparts increased flexibility and "softness" or hand to construct 10.

Figure 4:
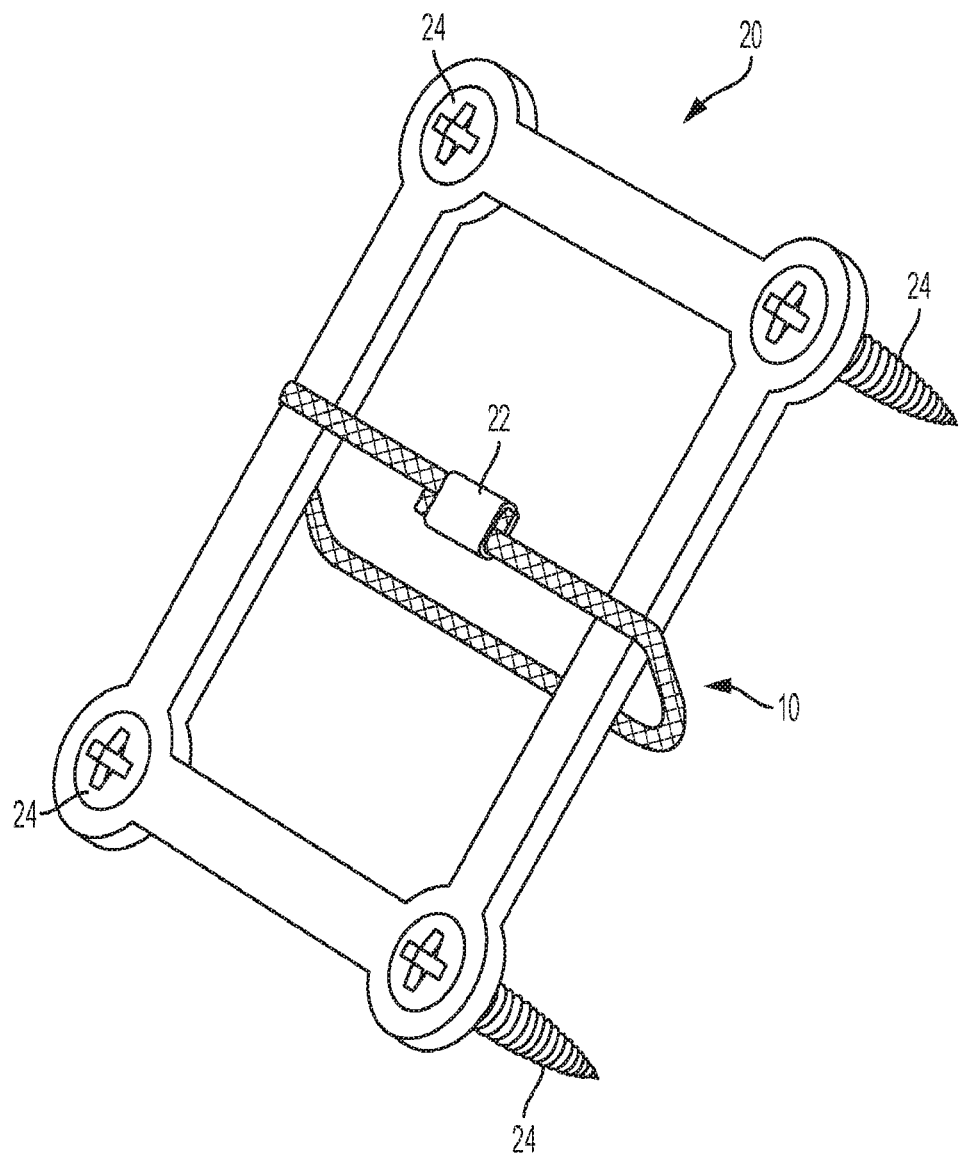
FIG. 4 is a perspective view of a sternotomy closure plate including a braided tubular construct in accordance with the present disclosure.

In an exemplary embodiment, construct 10 is sized and configured for use as a suture or other binding component in a surgical procedure. In one particular exemplary embodiment, construct 10 may be used as a closure cable for a sternotomy closure system, such as in conjunction with sternotomy closure plate 20 (FIG. 4) as further discussed below.

For example, construct 10 configured for use in such medical closure applications may have inner diameter $D_I$ (FIG. 1) between 0.010 inches and 0.200 inches, as determined by the outer diameter of the mandrel about which construct 10 is braided. The outer diameter $D_O$ follows from the diameter $D_C$ of constituent elements 12, namely, $D_O=D_I+2(D_C)$. Diameter $D_C$ of elements 12 may vary between 0.002 inches and 0.004 inches, for a range in outer diameter $D_O$ between 0.014 inches and 0.208 inches.

Moreover, the overall dimensions of the finished braid of construct 10 may also be influenced by the particular material used for strands 14 of elements 12. As discussed further below, a variety of metal material may be employed within the scope of the present disclosure.

In the context of orthopaedic and other applications, construct 10 confers a number of advantages as compared to woven or braided constructs using monofilament constituents. For example, constituent elements 12 using multiple strands 14 have increased flexibility as compared to a comparable monofilament, and the individual strands 14 can rearrange around one another to "self adjust" and lay flat when tensioned. This avoids or mitigates abrasion or cutting in an adjacent surface, such as sternal bone or tissue, and provides better load distribution to promote blood flow within the bone.

Construct 10 including multifilament constituent elements 12 also presents a smoother overall finish and feel, or "hand" as mentioned above, as compared to a monofilament braid or weave. At the same time, elements 12 can lay flat and substantially parallel to define a textured and consistent surface, which can form an effective anchor for swaged fittings and other friction-fit fittings, such as crimp 22 used in cerclage applications (FIG. 4), or end plugs used in some suturing applications. Because such a surface texture can be achieved without kinking or otherwise deforming the individual elements 12, this anchoring ability does not carry a penalty in the overall axial strength of the assembly as demonstrated in the Examples below.

The hollow tubular structure of construct 10 is orientation-independent, in that it can be expected to lay flat (FIG. 5B) when wrapped around an adjacent edge or surface (e.g., a bone) regardless of its rotational orientation. This orientation independence contrasts with other forms, such as such as ribbons or other flat constructs, which are orientation-dependent (e.g., the "sharp edge" of the ribbon must not contact the bone).

The braided or woven structure of construct 10 can be configured to reduce in diameter when placed under axial tension. This reduction allows construct 10 to be passed through standard crimping devices of the type already widely available for use with non-tubular braided materials (e.g., multifilament cables or "wire rope"), while also offering the advantages of the present multifilament design. Moreover, the present multifilament design is compatible with commonly-used surgical instrumentation, e.g., sternotomy closure instruments.

Braid and Strand Materials and Processing

As noted above, constituent elements 12 are made from metal strands 14. For purposes of medical devices, any biocompatible or implantable metal is a suitable candidate for strands 14, including: stainless steels such as 316LVM and 2205; cobalt-based and cobalt-chrome alloys including MP35N, 35N LT and L605; superelastic alloys including Nitinol (NiTi), NiTi ternary and quaternary alloys, and Titanium beta alloys; titanium alloys; and bioabsorbable metals including magnesium, zinc, iron and alloys thereof. Any of these metals may be formed as monolithic wires or composite wire materials, such as DFT (described above) and coated wire materials.

In production, strands 14 are first formed into individual multifilament constituent elements 12 by traditional methods such as twisting or wire-rope forming methods as noted above. Constituent elements 12 are then helically formed around a mandrel using traditional braiding techniques and equipment. At this point, thermal treatment may be applied to "set" or shape-set the elements 12 into the desired helical braided formation, such that internal diameter $D_I$ is maintained after the mandrel is removed. This shape-setting process may impart any of a variety of linear and/or curved configurations to the finished construct 10.

For example, a multi-diameter construct may be formed with one or more bulbous zones having outer diameters $D_I$ and $D_O$ larger at some axial locations as compared to other axial locations. In one embodiment, such a construct 10 may be formed with a regular recurrence of such bulbous zones in the manner of a sinusoidal outer profile, which can be used for enhanced tissue contact in some applications.

Further thermal stress relief may be applied as required or desired for a particular application. The final material of construct 10 may be fully annealed to be "soft," ductile and pliable, or may be thermally treated to retain a spring temper that is relatively stiffer and less pliable.

In an exemplary embodiment, construct 10 is subjected to thermal treatment at a temperature between 300° C. to 2100° C. for between 1 second and 1000 seconds. The specific time/temperature combinations is dependent on material and desired results, and can be modified as desired within the foregoing ranges to satisfy the needs of the application. The processing atmosphere should also be appropriate the particular alloy being treated, and may include Air, Hydrogen, Argon, Helium, or mixtures thereof.

Applications

As noted above and shown in FIG. 4, an exemplary application of construct 10 is in conjunction with sternotomy closure plate 20. In the illustrated embodiment, plate 20 may be secured to the sternum of a patient on both sides of an incision by bone screws 24, and further secured by wrapping construct 10 around plate 20 and the adjacent portions of sternum on both sides of the incision to form a cerclage. Crimp 22 may be used to secure the ends of construct 10 to close the loop, as illustrated. Advantageously, the use of construct 10 in this context minimizes the stress on the adjacent bone by maximizing surface area contact between the flattened and self-adjusted constituent elements 12 (FIG. 5B) and the adjacent bone or tissue surface.

Other applications for construct 10 include musculoskeletal fixation, such as securement of fractures in a hip or long bone. Construct 10 could also be used for ligament repair and sutures or other soft or hard tissue surgical fixation or closure devices.

Still other viable applications include pacing leads, which may in some cases need to make sharp turns and bear against an anatomic structure. Renal denervation is another application, in which construct 10 can be selectively axially tensioned to a smaller outer diameter $D_O$ and axially compressed to a larger diameter $D_O$ to allow for delivery through a catheter and controlled expansion once in the renal artery.

Additionally, construct 10 can be used as a stent structure designed for service in body lumens (vascular, gastrointestinal, renal, respiratory, or others). In particular, some stents are used in settings where relatively low radial forces are required and high deformation tolerance, compliance, and fatigue life is desirable. Construct 10 provides this combination of features and therefore can be suitable for stent applications.

Another application includes support structures for soft robotics components such as McKibben muscles, in which construct 10 can be inflated from within by pneumatic or hydraulic pressure to effect a larger outer diameter (e.g., diameter $D_O$ in FIG. 1A) and resultant axial contraction. In some embodiments, further tuning of the output of such a soft robotic application can be accomplished by the incorporation of thermally responsive shape memory alloy wires, such as wires made from nitinol or beta titanium, within the strand elements 12 of construct 10, thereby allowing alteration of the stiffness response by a change in material temperature. In still other embodiments, such temperature-sensitive elements 12 may be incorporated in a fluid-pressure-responsive construct to enable complex multiaxial motion through the combined influence of fluid pressure and temperature. In yet further embodiments, construct 10 could be built with monolithic polymer or metallic fibers, or with composite constructs such as polymer-insulated conductive elements, to provide electrical function via isolated conductive channels to power sensors or other electrical apparatus integrated with or connected to construct 10.

Still other non-medical applications include the use of construct 10 as a tensioning lace or binding element for sports equipment, such as ski boots, joint braces, helmets, skates and gloves where the flattening of the element provides even force distribution and a reduced tendency to slip or loosen with loss of tension. Such a lace or binding can be constructed with construct 10 in which strand elements 12 are a shape memory alloy, e.g., nitinol, capable of energy dissipation. In this application, the lace or binding element would function to provide holding force while also dissipating energy from a sudden application of force resulting, e.g., from an impact to the boot, brace, helmet or other structure retained on the user by construct 10. In this way, construct 10 can be used to dissipate energy applied to a user of the device, thereby guarding against injury.

EXAMPLES

The following non-limiting Examples illustrate various features and characteristics of the present invention, which is not to be construed as limited thereto.

In these Examples, exemplary braided, hollow metal bands in accordance with the present disclosure were produced, tested and characterized, particularly with regard to surface texture characteristics, crimp attachment strength and overall functionality in the context of a sternotomy suture application.

Example 1

Figure 3:
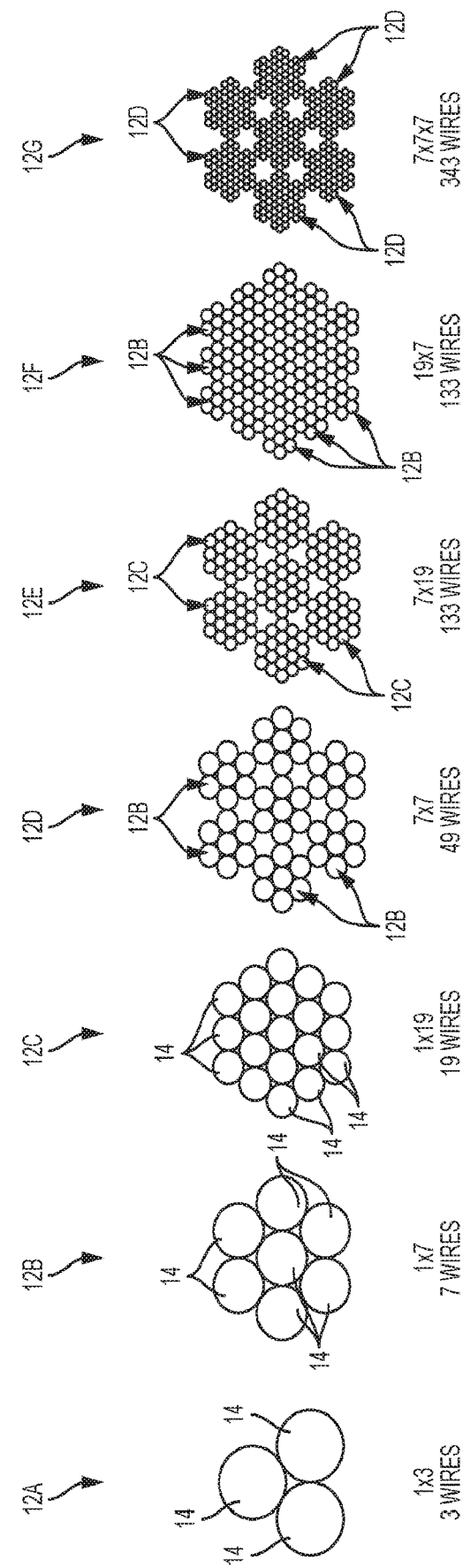
FIG. 3A is a cross-sectional view of a stranded wire in accordance with the present disclosure, having 3 individual wires making up the strands of the wire.
FIG. 3B is a cross-sectional view of another stranded wire in accordance with the present disclosure, having 7 individual wires making up the strands of the wire.
FIG. 3C is a cross-sectional view of yet another stranded wire in accordance with the present disclosure, having 19 individual wires making up the strands of the wire.
FIG. 3D is a cross-sectional view of a stranded cable in accordance with the present disclosure, having 7 sets of 7 individual wires for a total of 49 strands making up the cable.
FIG. 3E is a cross-sectional view of another stranded cable in accordance with the present disclosure, having 7 sets of 19 individual wires for a total of 133 strands making up the cable.
FIG. 3F is a cross-sectional view of yet another stranded cable in accordance with the present disclosure, having 7 sets of 19 individual wires for a total of 133 strands making up the cable.
FIG. 3G is a cross-sectional view of still another stranded cable in accordance with the present disclosure, having 7×7 sets of 7 individual wires for a total of 343 strands making up the cable.

A braided construct 10 using multifilament constituent elements 12 in accordance with the present disclosure was prepared from constituent stranded cables as described herein. 316LVM stainless steel was used for all strands 14, each of which was a "1×7" configuration as shown in FIG. 3B. Each strand 14 had a diameter of 0.0025 inches, for a total constituent diameter $D_C$ of 0.0075 inches. A total of thirty-two elements 12 were employed to make a braided construct having an outer diameter $D_O$ of 0.108 inches after braiding with a total of 224 individual monolithic wires in the form of strands 14.

Crimps 22 were affixed to the ends of the finished construct 10, and the crimped construct was subjected to tensile testing. "Breakload," i.e., the amount of tensile force required to dislodge one or both crimps 22, ranged from about 142 lbf to about 210 lbf. Table 1 illustrates the results of the tensile testing for this Example.

TABLE 1

Tensile Testing Results for a Braided Construct

| | Breakload (lbf) | Elongation (%) | Yield Load (lbf) | Visual Surface Prim |
|---|---|---|---|---|
| 1 | 142.565 | 12.8 | 2.246 | Ø.0635X.085" |
| 2 | 131.583 | 12.4 | 2.593 | Ø.0635X.085" |
| 3 | 198.782 | 5.6 | 3.709 | Ø.0635X.125" |
| 4 | 209.648 | 5.6 | — | Ø.0635X.125" |
| 5 | 158.049 | 15.4 | 5.516 | Ø.0635X.100" |
| 6 | 171.019 | 5.4 | — | Ø.0635X.100" |
| Mean | 168.608 | 9.5 | 3.516 | |
| Standard Deviation | 30.85813 | 4.51057 | 1.47225 | |
| Mean + 3 SD | 261.182 | 23.1 | 7.933 | |
| Mean − 3 SD | 76.033 | −4.0 | −0.901 | |
| Minimum | 131.583 | 5.4 | 2.246 | |
| Maximum | 209.648 | 15.4 | 5.516 | |

Figure 6:
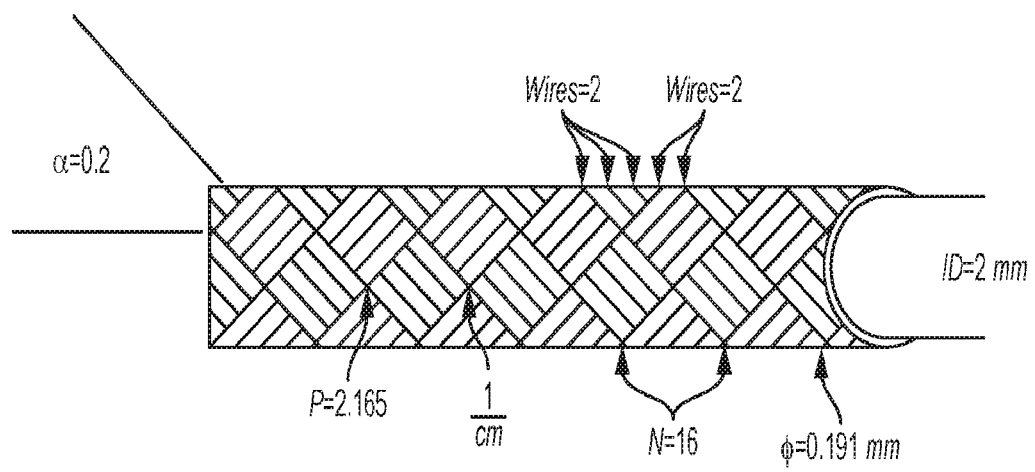
FIG. 6 is an elevation view of a braided construct made in accordance with the present disclosure, illustrating particular construct geometry and parameters.

Specifics of the wire material and configuration of the braided construct 10 used for the above-described test appears in Table 2 below, taken in conjunction with FIG. 6 which includes a pictorial representation of some of the variable employed in Table 2.

TABLE 2

Wire Material and Configuration for a Braided Construct

| Metric Units | | English Units |
|---|---|---|
| $\phi = 0.1905$ mm | Wire Diameter (input) | $\phi = 0.0075$ in |
| OD = 2.762 mm | Braid OD (input) | OD = 0.1087 in |
| ID = OD − 4·$\phi$ | Braid ID (calculation) | |
| ID = 2 mm | Braid ID or Mandrel Dia (calculated) | ID = 0.0787 in |

| Picks Per Centimeter | Pick Length | |
|---|---|---|
| $P = 2.17 \frac{1}{cm}$ OR | $P_l = \frac{1}{P}$ | $P = \frac{5.5}{in}$ |
| | $P_l = 4.62$ mm | $P_l = 0.182$ in |
| Wires = 2 | Number of wires per spool or bobbin aka "ENDS" (input) | |
| N = 16 | Number of spools/bobbins in machine aka "Carriers" (input) | |
| $\alpha = \text{atan}\left(\left(2 \cdot \pi \cdot (ID + 2 \cdot \phi) \cdot \left(\frac{P}{N}\right)\right)\right)$ | Braid Angle (output) | $\alpha = 0.2$ rad $\alpha = 11.446$ deg |
| $F = \frac{\text{Wires} \cdot P \cdot \phi}{\sin(\alpha)}$ | Braid Coverage Factor (output) | F = 0.416 |
| $K = (2 \cdot F - F^2)$ | Braid Coverage (output) | K = 65.9% |

Example 2

A braided construct using monofilament constituent elements was prepared as a control group. 316LVM stainless steel was again used for all the monofilament elements. Each element had a diameter of 0.0051 inches. A total of forty-eight monofilament elements were employed to make a braided construct having an outer diameter $D_O$ of 0.0984 inches after braiding.

Crimps 22 were affixed to the ends of the finished monofilament control construct, and the crimped construct was subjected to tensile testing. "Breakload," i.e., the amount of tensile force required to dislodge one or both crimps 22, ranged from about 25 lbf to about 52 lbf, all of which is substantially weaker than the breakloads observed in Example 1. Table 3 illustrates the results of the tensile testing for this Example.

TABLE 3

Tensile Testing Results for a Braided Construct

| Sample | Breakload (lbf) | Elong (%) | Yield Load (lbf) | Operator | Surface 1 | Surface 2 |
|---|---|---|---|---|---|---|
| 1 | 32.788 | 2.7 | 10.798 | EJS | Ø.068 | .080 LENGTH |

TABLE 3-continued

Tensile Testing Results for a Braided Construct

| Sample | Breakload (lbf) | Elong (%) | Yield Load (lbf) | Operator | Surface 1 | Surface 2 |
|---|---|---|---|---|---|---|
| 2 | 25.307 | 2.1 | 22.686 | EJS | Ø.068 | .080 LENGTH |
| 3 | 52.051 | 1.7 | 46.759 | EJS | Ø.0635 | .080 LENGTH |
| Mean | 36.715 | 2.1 | 26.747 | | | |
| Standard Deviation (SD) | 13.79813 | 0.49371 | 18.32132 | | | |
| Mean + 3 SD | 78.110 | 3.6 | 81.711 | | | |
| Mean − 3 SD | −4.679 | 0.6 | −28.217 | | | |
| Minimum | 25.307 | 1.7 | 10.798 | | | |
| Maximum | 52.051 | 2.7 | 46.759 | | | |

As shown in the above Examples, the construct 10 made in accordance with the present disclosure substantially outperformed a comparable monofilament design in turns of breakload for an end crimp While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A multifilament tubular construct, comprising:
a plurality of constituent elements woven or braided into a tubular cerclage cable defining an inner diameter, an outer diameter and an axial length in the absence of external forces, the constituent elements each comprising a twisted cable comprising:
a plurality of metal filaments having respective longitudinal axes each defining helices running substantially parallel to one another, such that the tubular construct is a flexible structure in both an axial direction and a radial direction, and the plurality of metal filaments can rearrange and self-adjust around one another to and lay flat when tensioned against a bone, whereby the multifilament tubular construct minimizes a stress on an adjacent bone or tissue surface by maximizing surface area contact between the flattened and self-adjusted metal filaments and the adjacent bone or tissue surface.

2. The multifilament tubular construct of claim 1, wherein the plurality of metal filaments of the constituent elements comprises between 2 filaments and 343 filaments.

3. The multifilament tubular construct of claim 1, wherein the inner diameter of the tubular construct is between 0.010 inches and 0.200 inches.

4. The multifilament tubular construct of claim 3, wherein the outer diameter of the tubular construct is between 0.014 inches and 0.208 inches.

5. The multifilament tubular construct of claim 1, wherein the plurality of constituent elements comprises between 8 and 128 constituent elements.

6. The multifilament tubular construct of claim 1, wherein the plurality of constituent elements define a plurality of picks at respective points of intersection between neighboring constituent elements, the picks numbering between 1 and 50 per inch of axial distance along an outer surface of the tubular construct.

7. The multifilament tubular construct of claim 1, further comprising at least one friction-fit fitting formed on at least one end of the tubular construct.

8. The multifilament tubular construct of claim 7, wherein the friction-fit fitting cannot be dislodged from the tubular construct by a separation force less than 142 lbf.

9. The multifilament tubular construct of claim 1, wherein at least one of the plurality of metal filaments of the constituent elements is formed of an absorbable metal.

10. The multifilament tubular construct of claim 9, wherein the absorbable metal comprises at least one of magnesium, zinc, iron and alloys thereof.

11. The multifilament tubular construct of claim 1, wherein at least one of the plurality of metal filaments of the constituent elements is formed of stainless steel.

12. The multifilament tubular construct of claim 1, wherein at least one of the plurality of metal filaments of the constituent elements is formed of a superelastic alloy.

13. The multifilament tubular construct of claim 12, wherein the superelastic alloy comprises Nitinol.

14. The multifilament tubular construct of claim 1, wherein at least one of the plurality of metal filaments of the constituent elements is formed of a cobalt-based or cobalt-chrome alloy.

15. The multifilament tubular construct of claim 1, wherein the tubular construct is configured to deform into a flattened shape when the tubular construct is bent or compressed around a surface, whereby the tubular cerclage cable is adapted to mitigate abrasion or cutting in an adjacent bone.

16. The multifilament tubular construct of claim 7, wherein the friction-fit fitting is deformed into contact with the plurality of metal filaments such that the friction-fit fitting is fixed to the tubular construct.

* * * * *